US00PP13367P2

(12) United States Plant Patent
Vlielander

(10) Patent No.: US PP13,367 P2
(45) Date of Patent: Dec. 17, 2002

(54) KALANCHOE PLANT NAMED 'GELAI'

(75) Inventor: Ike Vlielander, Maasland (NL)

(73) Assignee: Fides, Goldstock Breeding, B.V., Maasland (NL)

( * ) Notice: Subject to any disclaimer, the term of this patent is extended or adjusted under 35 U.S.C. 154(b) by 0 days.

(21) Appl. No.: 10/080,609

(22) Filed: Feb. 22, 2002

(51) Int. Cl.[7] ..... A01H 5/00
(52) U.S. Cl. ..... Plt./338
(58) Field of Search ..... Plt./338, 341, 339

(56) References Cited

U.S. PATENT DOCUMENTS

PP6,632 P * 2/1989 Drewlow ..... Plt./338
PP10,262 P * 2/1998 Jepsen ..... Plt./338

OTHER PUBLICATIONS

UPOV ROM GTITM Computer Database, GTI JOUVE retrieval software, 2002/02, citation(s) for "Gelai".*

* cited by examiner

*Primary Examiner*—Bruce R. Campell
*Assistant Examiner*—W C Baker
(74) *Attorney, Agent, or Firm*—C. A. Whealy

(57) ABSTRACT

A new and distinct cultivar of Kalanchoe plant named 'Gelai', characterized by its numerous yellow-colored flowers; upright and uniform plant habit; freely branching growth habit; dark green glossy leaves; early flowering; and excellent postproduction longevity.

1 Drawing Sheet

BOTANICAL CLASSIFICATION/CULTIVAR DESIGNATION

*Kalanchoe blossfeldiana* cultivar Gelai.

BACKGROUND OF THE INVENTION

The present invention relates to a new and distinct cultivar of Kalanchoe plant, botanically known as *Kalanchoe blossfeldiana*, and hereinafter referred to by the name 'Gelai'.

The new Kalanchoe is a product of a planned breeding program conducted by the Inventor in De Lier, The Netherlands. The objective of the breeding program was to create new freely-branching and freely-flowering Kalanchoe cultivars with attractive foliage and flower coloration.

The new Kalanchoe originated from a cross made by the Inventor in 1998 of the *Kalanchoe blossfeldiana* cultivar Gede, not patented, as the female, or seed, parent with the *Kalanchoe blossfeldiana* cultivar Alexandra, disclosed in U.S. Plant Pat. No. 10,262, as the male, or pollen, parent. The cultivar Gelai was discovered and selected by the Inventor as a flowering plant within the progeny of the stated cross in a controlled environment in De Lier, The Netherlands.

Asexual reproduction of the new Kalanchoe by terminal vegetative cuttings taken at De Lier, The Netherlands, since 1998 has shown that the unique features of this new Kalanchoe are stable and reproduced true to type in successive generations.

BRIEF SUMMARY OF THE INVENTION

The cultivar Gelai has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Gelai'. These characteristics in combination distinguish 'Gelai' as a new and distinct cultivar:

1. Numerous yellow-colored flowers.
2. Upright and uniform plant habit.
3. Freely branching growth habit.
4. Dark green glossy leaves.
5. Early flowering.
6. Excellent postproduction longevity.

Plants of the new Kalanchoe can be compared to plants of the female parent, the cultivar Gede. In side-by-side comparisons conducted by the Inventor in De Lier, The Netherlands, plants of the new Kalanchoe differed from plants of the cultivar Gede in the following characteristics:

1. Plants of the new Kalanchoe were more compact and less vigorous than plants of the cultivar Gede.

2. Plants of the new Kalanchoe had smaller and glossier leaves than plants of the cultivar Gede.

3. Flower color of plants of the new Kalanchoe was darker yellow than flower color of plants of the cultivar Gede.

4. Plants of the new Kalanchoe flowered earlier than plants of the cultivar Gede.

Plants of the new Kalanchoe can be compared to plants of the male parent, the cultivar Alexandra. In side-by-side comparisons conducted by the Inventor in De Lier, The Netherlands, plants of the new Kalanchoe differed from plants of the cultivar Alexandra in the following characteristics:

1. Plants of the new Kalanchoe had glossier leaves than plants of the cultivar Alexandra.

2. Plants of the new Kalanchoe flowered earlier than plants of the cultivar Alexandra.

Plants of the new Kalanchoe can also be compared to plants of the Kalanchoe cultivar Goldstrike, disclosed in U.S. Plant Pat. No. 6,632. In side-by-side comparisons conducted by the Inventor in De Lier, The Netherlands, plants of the new Kalanchoe differed from plants of the cultivar Goldstrike in the following characteristics:

1. Plants of the new Kalanchoe were more vigorous than plants of the cultivar Goldstrike.

2. Plants of the new Kalanchoe were more freely branching than plants of the cultivar Goldstrike.

3. Plants of the new Kalanchoe had glossier leaves than plants of the cultivar Goldstrike.

4. Flower color of plants of the new Kalanchoe was yellow whereas flower color of plants of the cultivar Goldstrike was yellow orange.

5. Plants of the new Kalanchoe flowered earlier than plants of the cultivar Goldstrike.

BRIEF DESCRIPTION OF THE PHOTOGRAPH

The accompanying colored photograph illustrates the overall appearance of the new Kalanchoe, showing the colors as true as it is reasonably possible to obtain in colored reproductions of this type. Colors in the photograph may differ slightly from the color values cited in the detailed botanical description which accurately describe the colors of the new Kalanchoe. The photograph comprises a side perspective view of a typical potted plant of 'Gelai'.

DETAILED BOTANICAL DESCRIPTION

In the following description, color references are made to The Royal Horticultural Society Colour Chart except where general terms of ordinary dictionary significance are used. Plants used for the aforementioned photograph and for the description were grown during the spring in De Lier, The Netherlands, in a glass-covered greenhouse. During the production of the plants, day temperatures ranged from 19 to 26° C.; night temperatures ranged from 20 to 21° C.; and light levels ranged from 10,000 to 50,000 lux. Unrooted cuttings were directly stuck in 12.5-cm containers and received long day/short night conditions (more than 14 hours of light) for about three weeks; plants then received photoinductive short day/long night conditions (minimum 14 hours (darkness) until flowering. Plants were about 15 weeks old from an unrooted cutting when the photograph and the description were taken.

Botanical classification: *Kalanchoe blossfeldiana* cultivar Gelai.

Parentage:

*Female or seed parent.*—*Kalanchoe blossfeldiana* cultivar Gede, not patented.

*Male, or pollen, parent.*—*Kalanchoe blossfeldiana* cultivar Alexandra, disclosed in U.S. Plant Pat. No. 10,262.

Propagation:

*Type cutting.*—Terminal vegetative cuttings.

*Time to initiate roots.*—Summer: About 10 days at 21° C. Winter: About 14 days at 21° C.

*Time to produce a rooted cutting.*—Summer: About 20 days at 21° C. Winter: About 27 days at 21° C.

*Root description.*—Numerous, fine, fibrous, and well-branched.

Plant description:

*Form.*—Upright and uniform plant habit. Very freely flowering with numerous compound cymes. Inverted triangle with rounded crown. Appropriate for 10 to 15-cm containers.

*Crop time.*—About 11 to 14 weeks: 2 to 4 weeks under long day/short night conditions followed by 8 to 10 weeks of short day/long night conditions. Vigorous growth rate.

*Plant height at flowering.*—About 21 cm.

*Plant diameter at flowering.*—About 19 cm.

*Branching habit.*—Freely branching; typically seven to eight lateral branches develop per plant. Pinching (removal of terminal apex) is not required but will enhance lateral branch development.

*Lateral branch description.*—Length: About 13 to 19 cm. Diameter: About 3 to 7 cm. Internode length: About 2 to 4 cm. Aspect: Erect. Strength: Moderately strong. Texture: Smooth, glabrous. Color: 147A.

*Foliage description.*—Leaves simple, opposite, generally symmetrical. Quantity per plant: About 8 to 13 mature leaves and 14 to 22 generative leaves. Length: About 11 cm. Width: About 8 cm. Shape: Ovate to elliptic. Apex: Obtuse. Base: Acute. Margin: Slightly crenate. Texture: Leathery, glabrous and succulent. Color: Developing and fully expanded leaves, upper surface; 147A; glossy. Developing and fully expanded leaves, lower surface: 147B. Venation, upper surface: 147A to 147B. Venation, lower surface: 147B. Petiole length: About 1.5 cm. Petiole diameter: About 4 mm by 8 mm. Petiole color: Upper surface: 147A to 147B. Lower surface: 147B.

Flower description:

*Flower type and habit.*—Single flowers arranged in compound dichasial cymes that arise from leaf axils. Freely flowering; more than 25 open flowers per lateral branch and more than 150 open flowers per plant. Flowering continuously for at least six weeks. Flowers persistent. Flowers not fragrant.

*Natural flowering season.*—Plants of the new Kalanchoe initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about eight to ten weeks are required. Actual time to flower is primarily dependent upon temperature and light intensity.

*Post-production longevity.*—Excellent post-production longevity; plants maintain good foliage and flower substance for about 48 days under environmental conditions. Individual flowers last about 18 days on the plant.

*Flower diameter.*—About 1.8 cm.

*Flower height.*—About 1.4 cm.

*Flower buds.*—Shape: Initially oblong, becoming tubular ovoid with development. Length: About 1.1 cm. Width: About 2.5 mm. Color: Initially, 138C, than 63D with development.

*Petals.*—Quantity: Four fused at base. Length: About 9 mm. Width: About 6.5 mm. Aspect: Flat to slightly upright. Shape: Ovate. Apex: Acute. Margin: Entire. Texture: Glabrous, smooth. Color: When opening, upper surface: 12A. When opening, lower surface: 12C to 12D. Fully opened, upper surface: 12B; color does not fade with subsequent development. Fully opened, lower surface: 12C to 12D.

*Sepals.*—Quantity: Four fused at base. Length: About 5 mm. Width: About 2 mm. Aspect: Erect. Shape: Oblong. Apex: Acute. Base: Obtuse to rounded. Margin: Entire. Texture: Glabrous, smooth. Color, upper and lower surfaces: 138D.

*Peduncles.*—Length: About 6 mm. Diameter: About 1 mm. Aspect: Erect. Strength: Strong, flexible. Texture: Smooth, leathery. Color: 138B.

*Reproductive organs.*—Stamens: Quantity per flower: Eight. Anther shape: Elliptic; flat. Anther size: About 0.3 mm. Anther color: Close to 150D. Pollen amount: Scarce. Pollen color: 12A. Pistils: Quantity per flower: Four. Style length: About 1 mm. Style color: 138D. Stigma shape: Flat, rounded. Stigma color: 8D. Ovary color: 138D.

*Seed.*—Length: About 0.1 mm. Diameter: About 0.05 mm. Color: Close to 166C.

Disease/pest resistance: Plants of the new Kalanchoe have not been observed to be resistant to pathogens and pests common to Kalanchoes.

Temperature tolerance: Plants of the new Kalanchoe have been observed to tolerate low temperatures of 12° C. and high temperatures of 35° C.

Garden performance: Plants of the new Kalanchoe perform have been observed to perform well in the garden and are tolerant to rain and wind.

It is claimed:

1. A new and distinct cultivar of Kalanchoe plant named 'Gelai', as illustrated and described.

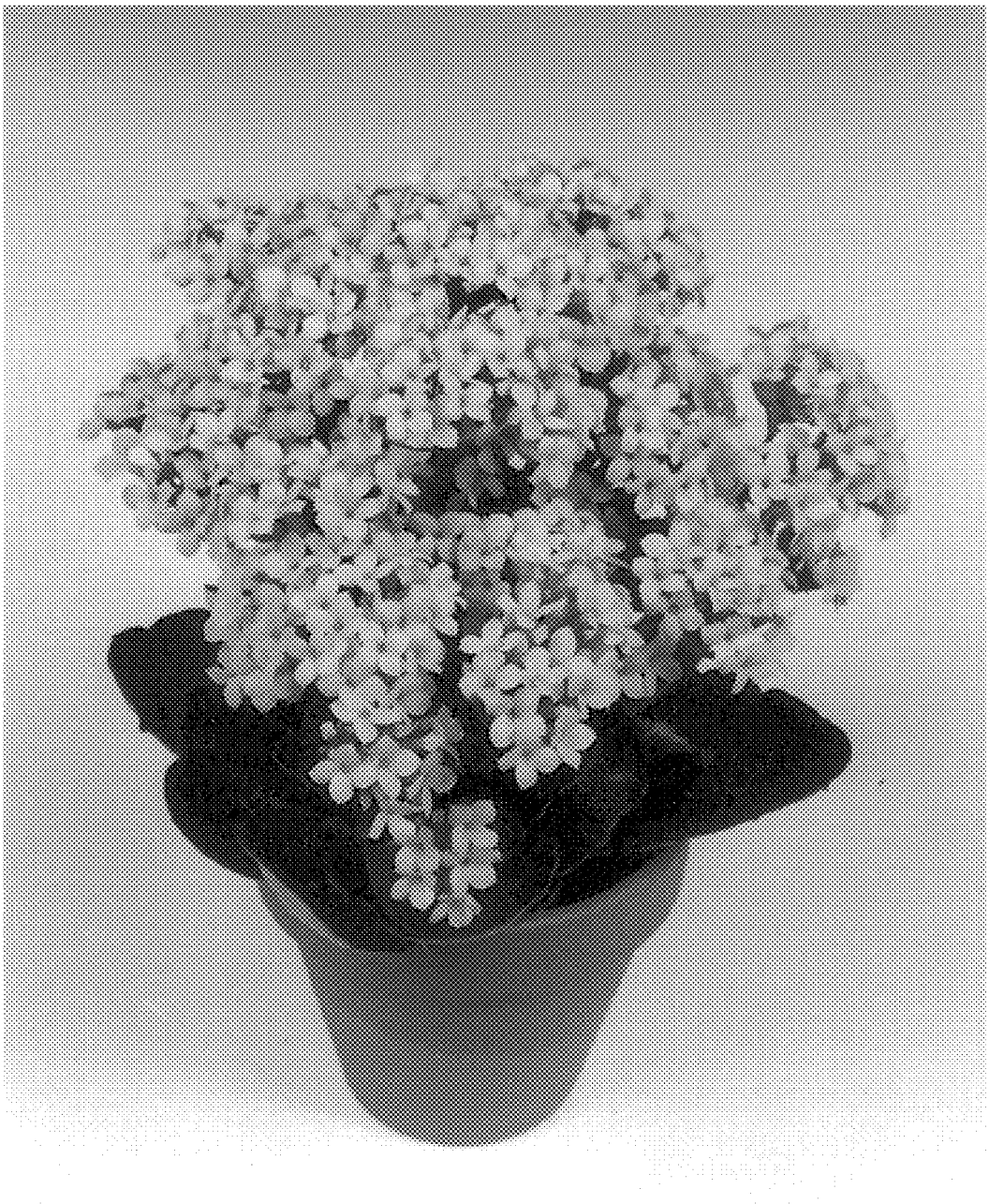

* * * * *